United States Patent [19]

Fischel

[11] Patent Number: 5,783,085
[45] Date of Patent: Jul. 21, 1998

[54] BLOOD FRACTIONATION METHOD

[75] Inventor: Halbert Fischel, Los Angeles, Calif.

[73] Assignee: Estate of William F. McLaughlin, Deerfield, Ill.

[21] Appl. No.: 655,292

[22] Filed: May 15, 1996

Related U.S. Application Data

[60] Continuation of Ser. No. 472,670, Jun. 7, 1995, abandoned, which is a division of Ser. No. 135,135, Oct. 12, 1993, Pat. No. 5,464,534, which is a continuation of Ser. No. 985,360, Dec. 2, 1992, abandoned, which is a continuation of Ser. No. 732,405, Jul. 18, 1991, abandoned, which is a division of Ser. No. 52,171, May 8, 1987, Pat. No. 5,034,135, which is a continuation of Ser. No. 449,470, Dec. 13, 1982, abandoned.

[51] Int. Cl.$^6$ .................... B01D 61/22; B01D 61/14; A61M 1/34
[52] U.S. Cl. ............... 210/651; 210/321.68; 210/650; 604/4
[58] Field of Search ..................... 210/651, 650, 210/652, 321.68; 604/4, 5

[56] References Cited

U.S. PATENT DOCUMENTS

| Re. 31,688 | 9/1984 | Popovich et al. | 210/90 |
|---|---|---|---|
| 1,664,769 | 4/1928 | Chance | 210/90 |
| 2,197,509 | 4/1940 | Reilly et al. | 210/297 |
| 2,398,233 | 4/1946 | Lincoln | 55/290 |
| 2,670,849 | 3/1954 | Dunmire | 210/360.2 |
| 2,709,500 | 5/1955 | Carter | 55/408 |
| 3,026,871 | 3/1962 | Thomas | 210/360.1 |
| 3,183,908 | 5/1965 | Collings | 261/DIG. 28 |
| 3,355,382 | 11/1967 | Huntington | 210/321.68 |
| 3,396,103 | 8/1968 | Huntington | 210/321.68 |
| 3,491,887 | 1/1970 | Maestrelli | 210/637 |

(List continued on next page.)

FOREIGN PATENT DOCUMENTS

| 1442874 | 11/1968 | Germany . |
|---|---|---|
| 52-18481 | 2/1977 | Japan . |
| 771142-5 | 10/1977 | Sweden . |
| 1283273 | 7/1972 | United Kingdom . |
| 1480406 | 5/1977 | United Kingdom . |
| WO 82/03568 | 10/1982 | WIPO . |

OTHER PUBLICATIONS

Smebly, The Taylor–Vortex Membrane Oxygenator;, Stratchchyde Bioengineering Seminars, Artificial Organs, University Park Press, RM Kenedi pp. 70–82, (undated).

Colten, "Fundamentals of Gas Transport in Blood", Artificial Lungs for Acute Respirator Failure–Theory and Practice, Zaplo & Qvist, Academic Press, NY, pp. 33–41 (1976).

Kitrilakis et al., "A Rotary Disk Membrane Oxygenator", Artificial Lungs for Acute Respiratory Failure–Theory and Practice, Zapol & Qvist, Academic Press, NY, pp. 211–221 (1976).

Kozinski et al., "Protein Ultrafiltration: A General Example of Boundary Layer Filtration", Alche Journal (vol. 18, No. 5) Sep. 1972, pp. 1030–1040.

(List continued on next page.)

Primary Examiner—John Kim
Attorney, Agent, or Firm—Daniel D. Ryan; Denise M. Serewicz; Bradford R. L. Price

[57] ABSTRACT

A system for separating at least one constituent from a liquid suspension such as blood induces high velocity flow by viscous drag about the circumference of a spinner having a filtration membrane with pore sized selected for the desired constituent. The high velocity circumferential flow is bounded by a spaced apart shear wall, with a spacing selected relative to the diameter of the spinner and its rotational velocity, also with respect to the viscosity of the suspension, to establish a flow within the shear gap, as substantial centrifugal forces are exerted upon the suspension. Under these conditions, in contact with the membrane and filtrate passes through the membrane is replenished with minimal adverse effects from deposition and concentration polarization, and with high efficiency because of high shear levels that are maintained. The filtrate is collected within the interior of the spinner in a conduit system and passed to an outlet orifice.

15 Claims, 7 Drawing Sheets

U.S. PATENT DOCUMENTS

| | | | |
|---|---|---|---|
| 3,523,568 | 8/1970 | Van Leeuwen | 55/290 |
| 3,568,835 | 3/1971 | Hansen | 210/86 |
| 3,634,228 | 1/1972 | Latham, Jr. | 210/427 |
| 3,647,440 | 3/1972 | Kitrilakis | 261/87 |
| 3,647,632 | 3/1972 | Johnson et al. | 261/87 |
| 3,705,100 | 12/1972 | Blatt et al. | 210/456 |
| 3,771,658 | 11/1973 | Brumfield | 210/321.3 |
| 3,771,899 | 11/1973 | Brumfield | 415/90 |
| 3,821,108 | 6/1974 | Manjikian | 210/321.1 |
| 3,830,372 | 8/1974 | Manjikian | 210/321.1 |
| 3,847,817 | 11/1974 | Jarman | 210/360.2 |
| 3,883,434 | 5/1975 | Gayler | 210/330 |
| 3,900,398 | 8/1975 | Gillette | 210/90 |
| 3,977,976 | 8/1976 | Spaan et al. | 210/87 |
| 4,040,965 | 8/1977 | Kohibes | 210/315 |
| 4,062,771 | 12/1977 | Saupe | 210/321.1 |
| 4,066,554 | 1/1978 | Guyer | 210/330 |
| 4,093,552 | 6/1978 | Guyer | 210/330 |
| 4,184,952 | 1/1980 | Stewart | 210/87 |
| 4,191,182 | 3/1980 | Popovich et al. | 210/90 |
| 4,212,741 | 7/1980 | Brumfield | 210/241 |
| 4,212,742 | 7/1980 | Solomon et al. | 210/456 |
| 4,535,062 | 8/1985 | Muller | 210/330 |
| 5,034,135 | 7/1991 | Fischel | 210/321.68 |

OTHER PUBLICATIONS

AK Bhagat/C.R. Wilke, "Filtration Studies with Ultrafine Particles", 9/66, University of California, Lawrence Radiation Laboratory, Berkeley, CA, UCRL–16574, preprint release for announcement in *Nuclear Science Abstracts*.

AK Bhagat/CR Wilke, "Engineering Analysis of the Rotofermentor", Aug. 1971, paper presented at annual meeting of the Soc. for Industrial Microbiology, Aug. 29–Sep. 4, 1971, Colorado State University.

W. Tobler, "Dynamic Filtration–The Engineering Concept of the Escher Wyss Pressure Filter." Nov/Dec 1979, *Filtration & Separation*, pp. 630–632.

J. Lieberherr, "Hydrodynamics of Annular Gap Flo Between Permeable Cylinder Walls", Escher Wyss Mitteilungen, Feb. 1978–Jan. 1979, 24–30.

A. Werynski et al., "Membrane Plasma Separation: Toward Improved Clinical Operation," Trans. Am. Soc. Artificial Internal Organs, vol. XXVII 1981, pp. 539–543.

K. Schindhelm et al.: Mass Transfer Characteristics of Plasma Filtration Membranes, *Trans Am. Soc. Artificial Organs*, vol. XXVII 1981, pp. 554–558.

Forstrom et al., Formed Element Deposition onto Filtering Walls, *Trans. Amer. Soc. Artificial Organs*, 21:602 (1974).

F. Castino et al., The Filtration of Plasma from Whole Blood: A Novel Approach to Clinical Detoxification, *Artificial Kidney, Artificial Liver, and Artificial Cells*, NE: Plenum Press, (undated).

A. Solomone et al., Continuous Flow Membrane Filtration of Plasma from Whole Blood, *Trans Amer. Doc. Artif. Internal Organs*, 24:21 (1978).

TB Wittbans et al., Filtration Plasmapheresis in Vivo,: *Tranfusion*, vol. 21, No. 5, pp. 502–510, (undated).

BA Solomon, "Membrane Solutions: Technological Principals and Issues", *Trans Am Soc Artif Internal Organs*, 1981, pp. 345–350.

Al Zydney et al., "Continuous Flow Membrane Plasmapheresis: Theoretical Modes for Flux & Hemolysis Prediction", *Trans Am Soc Artif Internal Organs*, pp. 408–412, (undated).

GI Taylor, "Stability of a Viscous liquid Contained Between Rotating Cylinders", *Phil Trans Roy Soc:* A, 223:289(1923).

GI Taylor, "Distribution of Velocity & Temperature Between Concentric Rotating Cylinder", *Phil Trans Roy Soc:* A, 151:494 (1932).

J. Schlichting, "Boundary–Layer Theory", pp. 500–509, 521–522, McGraw–Hill, NY 1968.

Al Robinson, "How Does Fluid Flow Become Turbulent", *Science*, 221:140, Jul 1983.

JDS Galyor et al., Gas Transfer & Thrombogenesis in an Annular Membrane Oxygenator with Active Blood Mixing, vol. XIX, *Trans Am Soc Artif Organs*, 1973 pp. 516–524.

TM Wood Thesis in Deposition of Red Blood Cells onto Filtering Surfaces, Univer. of Minn. 1914.

AB Strong et al., "An Experimental Study of Mass Transfer in Rotating Coneote Flow with Low Axial Reynolds Number", *The Canadian Journal of Chem. Eng.*, vol. 54, Aug. 1976, pp. 295–298.

EC Eckstein et al., Self–Diffusion of Particles in Shear Flow of a Suspension J. Fluid Mech (1970) vol. 79 part a., pp. 191–209.

TK Sherwood et al., "Desalination by Reverse Osmosis", Fundamentals vol. 6, No. 1, Feb. 1967, pp. 2–12.

Hallstrom & Lopez–Leiva, "Description of a Rotating Ultrafiltration Module" *Desalination*, Netherlands 24 (1978) 273–279.

Lopez–Leiva, "Ultrafiltration at Low Degrees of Concentration Polarization, Technical Possibilities", *Desalination*, Netherlands 1980.

KA Klaus, "Cross Flow Filtration and Axial Filtration", (unknown original and date) pp. 1059–1075.

CR Wilke et al., "Filtration Studies with Ultrafine Particles", University of California UCRL–16574 Sep. 1966, p. 106.

Lopez–Leiva PH.D. Dissertation, "Ultrafiltration in Rotary Annular Flow."Dec. 1979, Div. of Food Eng., Lund University, Sweden.

W. Tobler, "Dynamic Filtration: Principal & Application of Shear Filtration in an Annular Gap", *Filtration & Separation*, Jul. 8, 1982 pp. 329–333.

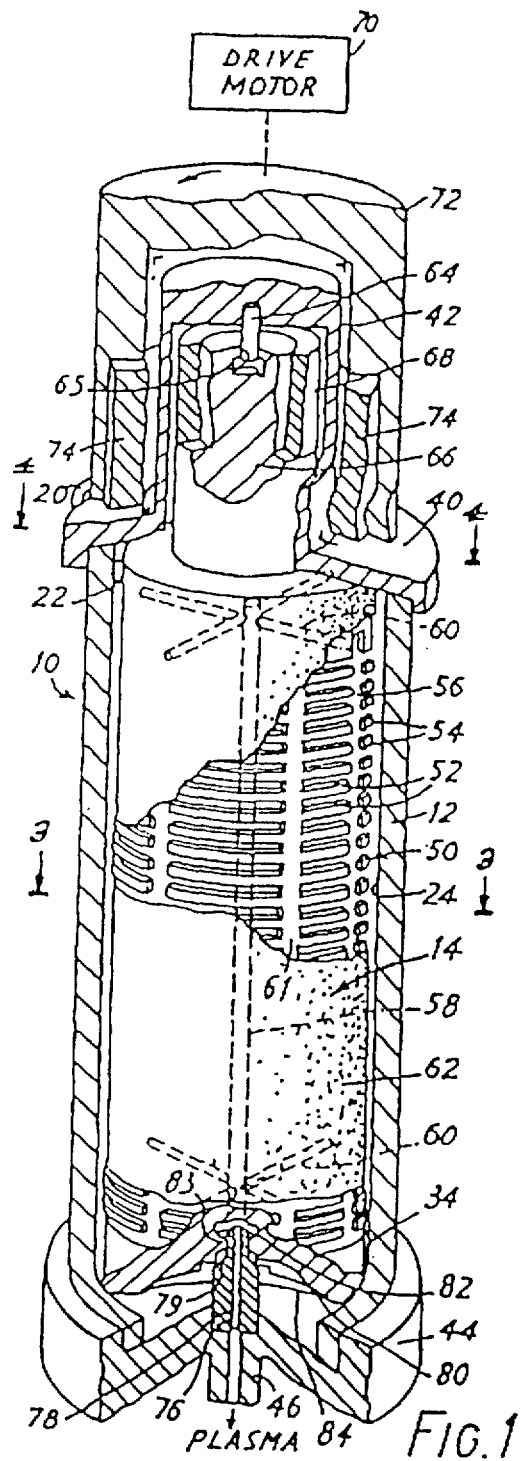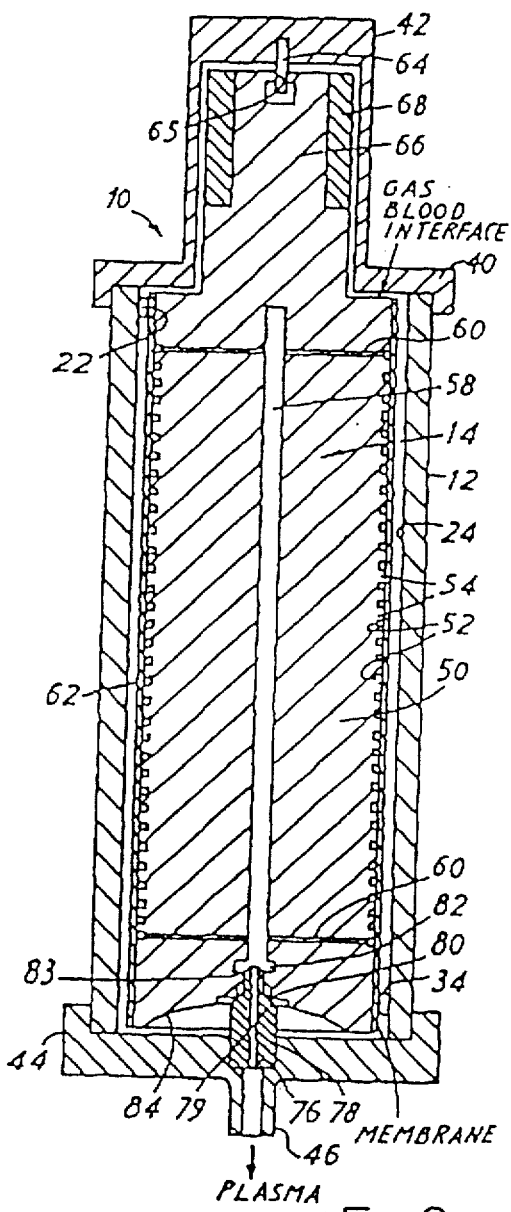

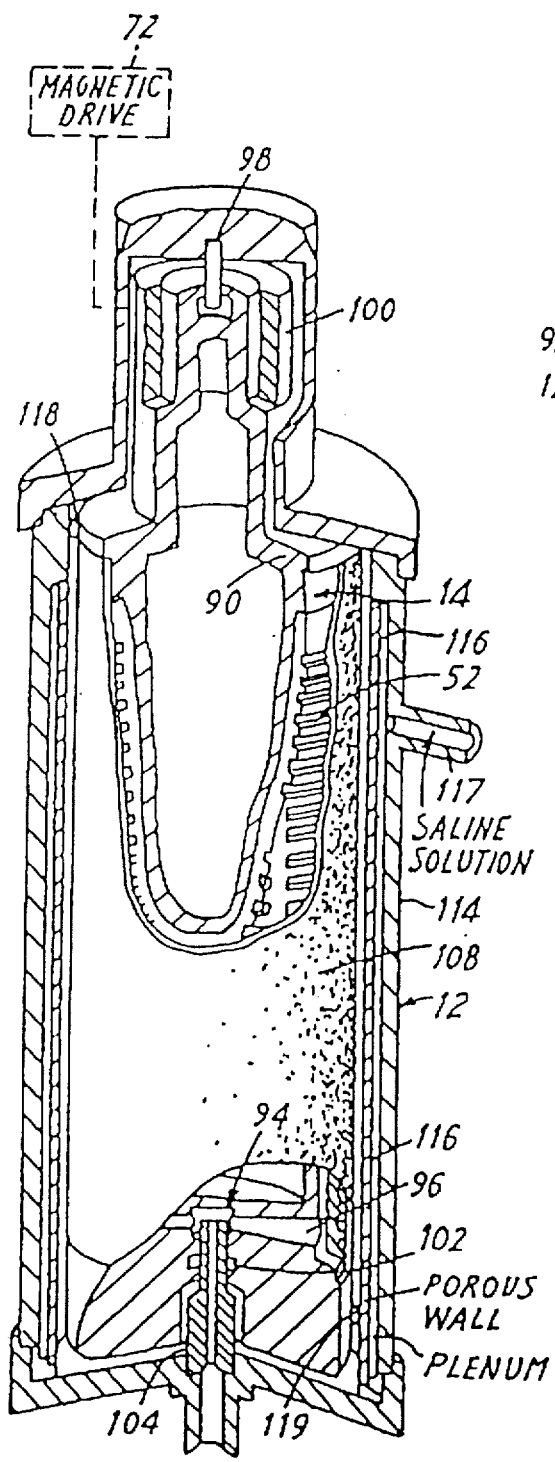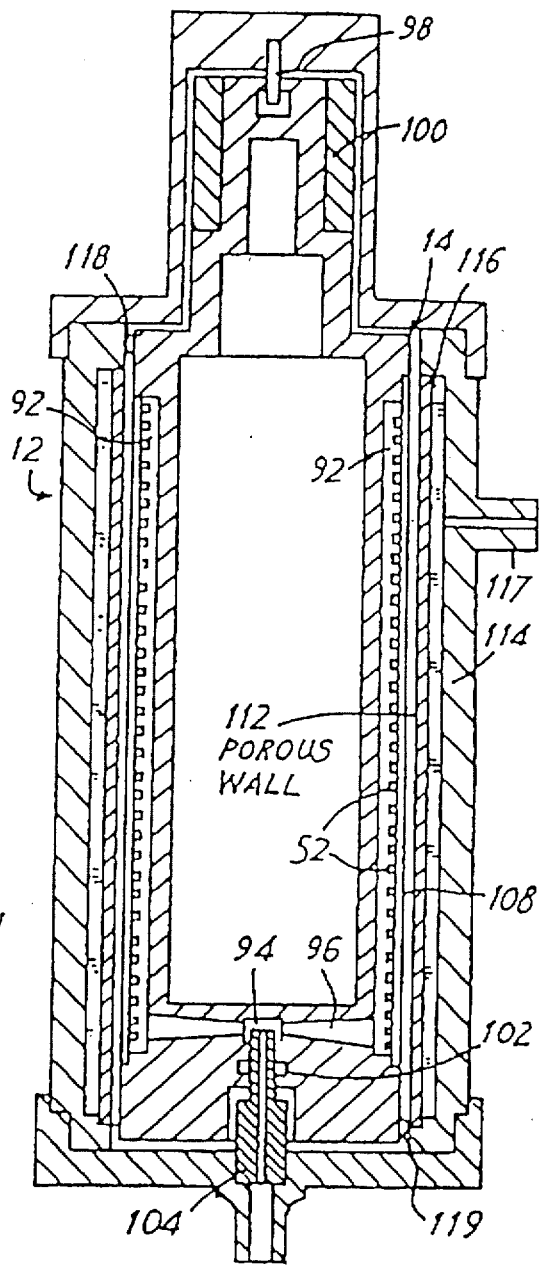

BLOOD FRACTIONATION METHOD

This is a continuation of application(s) Ser. No. 08/472,670 filed on Jun. 7, 1995, abandoned, which is a divisional of application Ser. No. 08/135,135 filed Oct. 12, 1993, now U.S. Pat. No. 5,464,588; which is a continuation of Ser. No. 07/985,360 filed Dec. 9, 1992 (abandoned); which is a continuation of Ser. No. 07/732,405 filed Jul. 18, 1991, abandoned; which is a divisional of application Ser. No. 07/052,171 filed May 8, 1987 (now U.S. Pat. No. 5,034,135); which is a continuation of application Ser. No. 06/449,470 filed Dec. 13, 1982 (abandoned).

BACKGROUND OF THE INVENTION

Blood is a living, complex, and in many respects unstable system, and any processes which seek to separate or affect the characteristics of its constituents must be carried out with due concern for these properties. Many medical procedures are based upon the separation of whole blood into particular constituents, whether processing homogeneous masses such as plasma or extracting formed or discrete elements such as red blood cells, platelets and leukocytes. More recently there has been a great increase in therapeutic treatments (therapeutic apheresis) in which different components in the blood complex can be processed or removed to attenuate diseases or destroy harmful organisms. The separation of the constituents of whole blood, without damage, is fundamental to the plasma collection industry, therapeutic apheresis, and numerous biomedical procedures. Blood separation processes have been widely investigated and discussed in the scientific and patent literature, not only because of their importance but because they present particularly critical and difficult examples of the general problem of separating and removing suspended constituents from a solution.

Workers in the art have relied on one of two fundamentally different approaches, namely centrifugation and membrane separation, to separate the constituents of blood. Centrifugation, or stratification under the influence of centrifugal forces, may be realized on a continuous as well as a batch basis. Adequate centrifugation intervals provide a high degree of stratification and high yields. For continuous centrifugation a probe or other separator mechanism in the path of a particular layer (e.g. plasma) removes the selected constituent. However, long residence times, typically several minutes to several hours, and sometimes objectionable additives as well are required for sharply defined stratification. Even with long residence times some residual concentration of cells may remain in the plasma or extracted cellular component. In addition, rotating seals must be used that are exposed to the liquid in such a way that they present difficulties with insterility, leakage and contamination. The presence of a probe or other outlet in a continuous centrifuge system requires some membrane or filter shielding to prevent drawing off undesired constituents with the selected stratified layer. Because such a membrane or filter becomes exposed to a highly concentrated cellular mass that tends to be drawn toward the orifice, and because of the active propensity of blood constituents for adhering to and coating foreign substances, plugging or blocking of the conduits ultimately occurs.

Centrifugation can be used to obtain in excess of 90% recovery of a selected constituent such as plasma, and is the most widely employed system despite the problems mentioned and the manual steps required. Some commercial hemapheresis systems are based upon membrane filtration techniques because disposable modules can be used to provide essentially cell free fluid separations quite rapidly. Filtration rates and recoveries have been improved by flowing whole blood tangential to a membrane, with viscous shear acting on the flow so as to prevent red cells (in the case of plasma extraction) from exuding into the membrane pores to plug them. The application of the shear principle to separation of blood, previously known in other fields, was apparently first proposed for the separation of plasma by Blatt et al in an article entitled "Solute Polarization and Cake Formation in Membrane Ultrafiltration: Cause, consequences and control techniques", in *Membrane Science and Technology*, Plenum Press, N.Y. 1970, pp. 47–97, and by Blatt in U.S. Pat. No. 3,705,100. Intensive investigation of the literature has led to widely recognized understandings that certain parameters are crucial. These are the shear rate, the hematocrit (percentage of cells), plasma flux per unit area, transmembrane pressure, blood flow resistance, sieving coefficient (percent of species transmitted) and hemolysis (measured as percent hemaglobin in plasma). The limiting factors on performance are regarded in the literature as being deposition or "fouling" and polarization concentration. The former factor pertains to the plugging of membrane pores by the entrapment or adhesion of cellular or protein matter, or both, and the latter relates to the limits imposed on transport of blood constituents when a high concentration of suspended matter exists near the membrane. As plasma is withdrawn from whole blood the hematocrit increases so that with 90% plasma recovery and a hematocrit of 50%, for example, the return to the donor is about 91% cells, which comprises an extremely concentrated cell mass. Even with the best designed prior art systems, the flow of plasma through the membrane is more than approximately two orders of magnitude smaller than would be the flow through a membrane exposed only to pure plasma. The formed elements in suspension in the blood clearly are the cause of such limitations. In consequence, large membrane areas are required to recover relatively modest amounts of plasma (e.g. 50% of inflowing plasma for hematocrits below 40%, with top yields of 20 to 30 ml/min) and the efficiencies of these systems are even lower for donors having normal hematocrit levels (37 to 47 for females and 40 to 54 for males). The technique, sometimes used, of diluting blood to substantially lower hematocrit levels by the use of anticoagulants, is undesirable both for the collected plasma and for the donor.

Much attention has been paid to the shear rate and a number of low shear devices (below 1000 $sec^{-1}$) of large area are now in use. These devices have been described by workers such as Werynski et al in an article entitled "Membrane Plasma Separation—Toward Improved Clinical Operation" in *Trans. Am. Soc. Art. Int. Organs*, 27: 539–42 (1981), and Schindhelm et al in "Mass Transfer Characteristics Of Plasma Filtration Membranes" published in *Trans. ASAIO*, 27: 554–8 (1981). The articles indicate that the low shear systems, typically with shear rates of 500 $sec^{-1}$ or less, are limited primarily by concentration polarization. At the opposite limit, for high shear devices (e.g. greater than 2000 $sec^{-1}$) as discussed in detail by Blatt, cited above, deposition is the limiting factor. This conclusion is supported by an article by Castino et al in Publication No. 395, Blood Research Laboratory, American National Red Cross, (also published as Final Report NA/BL Contract No. 1-HB6-2928) entitled "Microporous Membrane Plasmapheresis", by an article entitled "Continuous Flow Membrane Filtration Of Plasma From Whole Blood" by Solomon et al in *Trans. ASAIO*, 24: 21 (1978), by U.S. Pat. No. 4,191,182 to Popovich, and by U.S. Pat. No. 4,212,742 to Solomon.

Despite widespread and intensive study of high shear systems, however, there has been little commercial use thus far, and upon analysis this appears to be due to a number of conflicting factors. A reasonable plasma recovery (e.g. 75%) demands excessive membrane area because, among other things, as hematocrit increases plasma flux efficiency falls, while blood viscosity increases substantially. To overcome these factors by increasing shear would require overly high blood flow rates obtained, as in Castino or Solomon cited above, by recirculating the blood. Also excessively small gap dimensions would be needed along with obligatory high transmembrane pressure due to blood flow resistance. Such systems are thus inherently limited in capability while the low shear high area systems are expensive when adequately sized.

After extensive work on and analysis of blood separation problems, including plasma collection, applicant has devised a blood separation technique in which a rotary concentric membrane structure imparts angular velocity to the interior surface of an annular blood volume bounded closely on the opposite side by a concentric stationary wall. Remarkable improvements are achieved in terms of plasma recovery rates, plasma purity, independence from hematocrit level, speed of operation and cost. The system and method drastically differ from both the centrifugation and the membrane filtration techniques previously utilized in this field.

Subsequent to applicant's discoveries and development work, applicant has undertaken a broad search of the patent and scientific literature in order to acquire a more comprehensive understanding of the relationship of his system to apparatus and methods used in other fields. A significant number of disclosures have been found which spin a rotatable filter drum or cylinder within a bath of a liquid system in which other material (e.g. sediment or particle matter) is entrained or suspended. The spinning is used to throw off higher density particulates and suspended matter that impinge upon and plug the filter. The following patents comprise examples of this approach:

| U.S. Pat. No. 1,664,769 | Chance | 1928 |
| U.S. Pat. No. 2,197,509 | Reilly et al | 1940 |
| U.S. Pat. No. 2,398,233 | Lincoln | 1946 |
| U.S. Pat. No. 2,709,500 | Carter | 1955 |
| U.S. Pat. No. 3,355,382 | Huntington | 1967 |
| U.S. Pat. No. 3,491,887 | Maestrelli | 1970 |
| U.S. Pat. No. 3,568,835 | Hansen | 1971 |
| U.S. Pat. No. 3,821,108 | Manjikian | 1974 |
| U.S. Pat. No. 3,830,372 | Manjikian | 1974 |
| U.S. Pat. No. 3,833,434 | Gayler | 1975 |

There have also been various investigations in other fields of the use of a rotating filter member in conjunction with an outer wall for purposes of imposing shear, examples of which are as follows:

"Description of a Rotating Ultrafiltration Module", B. Hallstrom et al in *Desalination* (Netherlands) Vol. 24, pp. 273-279 (1978).

"Ultrafiltration at Low Degrees of Concentration Polarization: Technical Possibilities", M. Lopez-Leiva in *Desalination*, Vol. 35, pp. 115-128 (1980).

These two publications relate to the handling of solutions, rather than suspensions, and induce shear solely for specific purposes, such as reverse osmosis. Centrifugation is not an operative factor in these systems.

The patents and publications listed above are derived from a wide spectrum of arts and technologies which are often nonanalogous, even to each other. They primarily deal with stable liquid systems which can be treated strenuously without harmful effects. The teachings of these different publications thus cannot be translated to the myriad problems involved in the separation or fractionation of blood constituents. The danger of trauma, the particular adherent qualities of blood, and the significant changes in properties that arise as a separation process proceeds all characterize blood fractionation problems as not only critical but in fact unique.

Applicant also points out that the broad field of blood processing includes oxygenation techniques, and that some oxygenation systems incorporate rotating membranes, as described in:

"An Experimental Study of Mass Transfer in Rotating Cuvette Flow with Low Axial Reynolds Number" by Strong et al. in *Can. Jnl. of Chem. Enq.*, Vol. 54, pp. 295-298 (1976).

| U.S. Pat. No. 3,674,440 | Kitrilakis | 1972 |
| U.S. Pat. No. 3,183,908 | Collins et al | 1965 |
| U.S. Pat. No. 3,026,871 | Thomas | 1962 |
| U.S. Pat. No. 3,771,658 | Brumfield | 1973 |
| U.S. Pat. No. 3,771,899 | Brumfield | 1973 |
| U.S. Pat. No. 4,212,741 | Brumfield | 1980 |

These patents illustrate some of the special care and expedients that must be employed in handling blood, but they propose and utilize techniques which have previously been considered inimical to blood separation objectives, such as flow vortices and other non-laminar effects.

SUMMARY OF THE INVENTION

Systems and methods in accordance with the invention for separating constituents of blood subject a thin flow sheet of blood to force for a sufficient time to create a concentration gradient of blood constituents while concurrently establishing high shear across the sheet. A moving membrane in contact with the flowing blood and concentric with a spinning axis generates both centrifugal force and high shear on the blood flow through viscous drag. The membrane concurrently filters the desired medium solely from the adjacent flowing mass. Radial migration of cellular matter outwardly causes replenishment of lighter filtrate at the membrane surface to maintain the concentration gradient despite constant recovery of filtrate. The thin flow sheet is configured as an annulus between rotating member, concentric about a central axis, and a stationary concentric shear wall, and moves longitudinally between entry and exit regions as well as circumferentially about the member. The filtrate, essentially free of higher density constituents, passes readily through the membrane and via the interior of the rotating member into an outflow path. This action increases filtrate recovery for a given membrane area by more than an order of magnitude while virtually eliminating deposition and concentration polarization limitations. Low cost disposables in accordance with the invention process whole blood from a donor continuously without damaging the fragile unstable, blood system. Furthermore, the inlet and outlets are fixed elements and the internal flow paths are such that the flow paths are sterile and not subject to external contamination.

Usage of a rotating concentric filtration membrane that is bounded by a concentric shear wall is applicable to a number of systems for separating liquid suspensions. High rotational rates in association with small gaps generate flow in which a radial concentration gradient and high shear are both obtained.

As the following description demonstrates, the invention serves to filter blood without damage to red blood cells, leukocytes, or platelets. It is well known that these cellular components of blood are enclosed only by an outer phospholipid bilayer membrane that is not rigid and that can be ruptured relatively easily by mechanical forces. It is also well known that the same type of membrane structure, having sensitivity to trauma, is common to a large class of biological cells, including all animal cells, such as human blood and tissue cells and vertebrate and invertebrate blood and tissue cells.

The effect becomes noticeable for blood when the rotational rate, the viscosity of the liquid complex, the residence time in the annular separation zone, i.e. the concentric gap within which the blood flow is confined, establish conditions within the system with shear in excess of $1000^{-1}$, and centrifugal forces at the membrane surface of greater than 50 gravities (g's). The permissible operating regimes are stable, but relatively narrow, for blood. For separation of plasma, for example, superior results in terms of cost-performance characteristics are achieved by using small membrane area in a low cost disposable module. In one practical example, using a 2.54 cm (1") diameter spinner and a 50 $cm^2$ membrane area, a gap dimension of 0.06 cm (0.024") to 0.09 cm (0.037") is employed with rotational speeds of about 3600 r.p.m. Under such conditions, and with normal blood viscosity typical of 45 hematocrit blood, the shear is in a safely conservative range of 8000 $sec^{-1}$ or less, and residence time and dynamic forces are sufficient for greater than 90% recovery of pure plasma from a blood flow rate of 60 ml/min to about 78% recovery from a flow of 100 m/min. Thus numerous, often conflicting requirements are concurrently satisfied: shear must be high enough for efficient filtration but not so high as to damage red cells or other matter; dynamic forces must be adequately high to separate different density constituents without inducing excessive shear; filtration efficiency must not deteriorate substantially with time; the residence time must be adequate for high recovery; and the changing viscosity of the blood stream cannot cause a local variation from these conditions.

In a more specific example of a system for separating constituents of blood, a central spinner may be disposed along a vertical central axis, within an outer confinement vessel whose inner wall defines a shear wall that is concentric with and spaced apart from the spinner surface by the shear gap. The spinner body includes surface grooves communicating through interior passageways with a central plasma manifold or conduit, and the spinner surface is covered by a membrane having a pore size selected for the desired filtrate, such as 0.4 to 0.8 μm for plasma. The spinner is rotated at the desired rotational velocity as blood is fed tangentially inwardly into the gap. The lower density filtrate passes through the membrane pores under transmembrane pressure established by static pressure within the system, with filtration efficiency being markedly augmented by high shear. Constituents filtered through the membrane are collected within the interior of the spinner at a central manifold and passed out via a central orifice in the rotary seal at the lower end of the chamber. High density constituents move longitudinally downwardly under flow pressure and gravity to pass out of the shear gap region directly into a tangential exit orifice. The spinner is indirectly driven by a magnetic coupling at the upper end from an exterior motor driven structure to a magnetic ring on the spinner body. The exterior and interior magnetic elements of the drive coupling may be longitudinally displaced so that magnetic forces constantly exert a downward force on the spinner body, seating it firmly against the rotary bottom seal. The seal functions only to separate the blood and plasma sides of the membrane, and the sterility of the blood path therefore is not dependent on seal operation. Alternatively the magnetic elements can be centered so that the spinner is suspended in the magnetic field, and the seal can be established about the bearing circumference. The longitudinal ends of the spinner body are juxtaposed closely adjacent to the confinement vessel end walls, and air within the system is stably trapped in small volumes having limited gas-liquid interface area that isolate the rotary bearings at each end of the spinner. Those parts that contact blood, such as the spinner body and confinement vessel, may be of molded plastic and of small size, and of low cost because expensive rotary bearings and seals are not required. Consequently the unit apart from the external magnetic drive is a disposable which can be used with a single donor, to collect plasma and return undamaged high hematocrit suspension.

A different usage of the concept arises rom applications in which frozen concentrated red cells are stored along with white cells and white cell aggregates in toxic anti-freezing solutions for prolonged periods. Here the outer confinement wall of the shear gap may be porous, to provide a large surface area for entry of a saline solution. As the toxic solution carries the mass of concentrated red cells and accompanying matter through the shear gap, the constantly introduced saline bath and the toxic solution which it dilutes includes the white cells and white cell aggregates. This matter is continuously extracted through a filtration surface having relatively large pore size (e.g. 70–100 μm). At the outlet end of the system is derived a fully washed red cell flow, which may e of lowered hematocrit through the controlled addition of saline solution.

The capabilities of systems in accordance with the invention may be utilized to great advantage in blood fractionation systems. In the collection of plasma, for example, the membrane area can be a small fraction of the area of membranes currently used, while providing a recovery efficiency, i.e., percent of inflowing plasma component actually recovered, in the range of 80% to 90% and recovery completions within times compatible with the rates at which blood can be taken from a donor. Furthermore the system can function substantially independently of the age and hematocrit of the blood being processed. The concepts of the invention include not only plasma separation apparatus and methods, but disposable filtration units, and instrumented plasma collection control as well.

BRIEF DESCRIPTION OF THE DRAWINGS

A better understanding of the invention may be had by reference to the following description, taken in conjunction with the accompanying drawings, in which:

FIG. 1 is a perspective view, partially broken away, of a plasma collection apparatus in accordance with the invention;

FIG. 2 is a side sectional view of the apparatus of FIG. 1;

FIG. 7 is a perspective view, partially broken away, of a variation of the system of FIG. 1, useful for washing a concentrated red cell mass of accompanying white cells and toxic anti-freezing solution;

FIG. 8 is a side sectional view of the arrangement of FIG. 7;

DETAILED DESCRIPTION OF THE INVENTION

Figure 3:
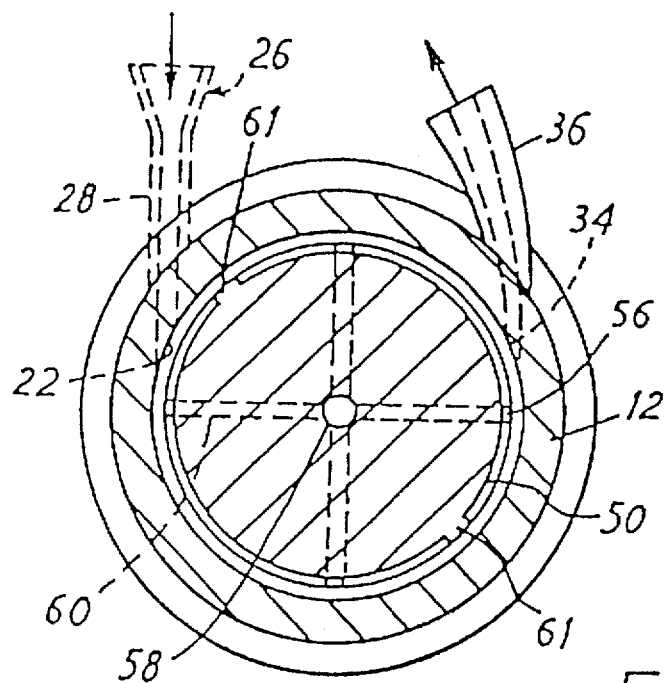
FIG. 3 is a top sectional view of the apparatus of FIG. 1, taken along the line 3—3 in FIG. 1 and looking in the direction of the appended arrows.
Figure 4:
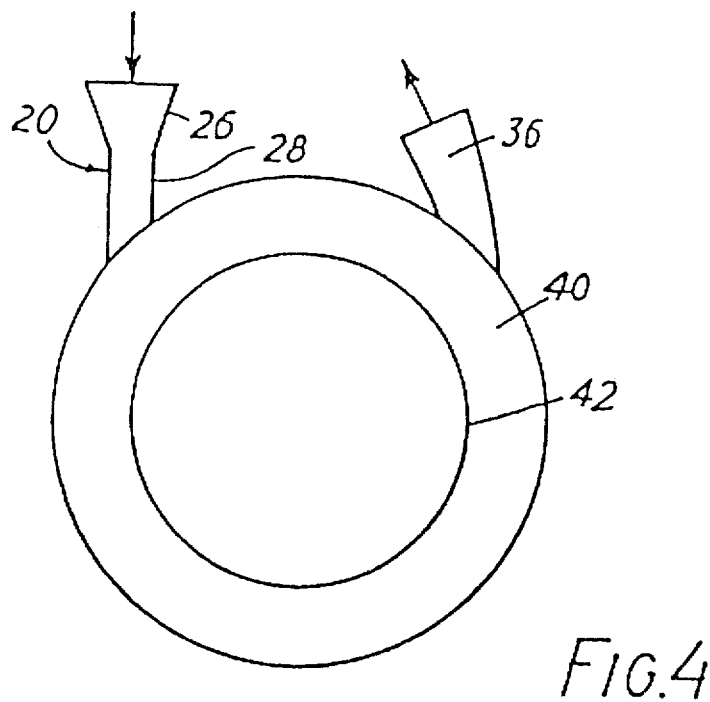
FIG. 4 is a top sectional view of a portion of the apparatus of FIG. 1, taken along the line 4—4 in FIG. 1 and looking in the direction of the appended arrows.

A blood fractionation system 10 in accordance with the invention, referring now to FIGS. 1-4 extracts plasma from whole blood quickly and at low cost in the quantities typically derived from an individual human donor. Only the plasma separation device and the associated drive unit are shown, for ease of understanding, although an associated control and instrumentation system is described hereafter. It should particularly be noted, however, that the system meets the need for a disposable module that is so low in cost that it need be used only once. In these Figures, relative sizes cannot be depicted with clarity and it should be expressly recognized that the drawings are not to scale. Gap sizes and membrane thicknesses particularly are exaggerated for better understanding.

The system 10 includes principally a generally cylindrical housing 12, mounted concentrically about a longitudinal, vertical central axis, and an internal rotary spinner 14 also mounted concentric with the central axis and rotatable concentrically within the cylindrical housing 12. The boundaries of the blood flow path are defined by the interior surface of the housing 12, and the exterior, spaced apart, surface of the rotary spinner 14, the spacing between which is sometimes referred to as the shear gap for this example. Whole blood is fed from an inlet conduit 20 through an inlet orifice 22 which directs the blood into the blood flow entrance region in a path tangential to a circumference about the upper end of the rotary spinner 14. The inner wall 24 of the housing 12 lies in a right circular cylinder spaced at a uniform distance, here approximately 0.024"(0.06 cm) from the outer circumference of the rotary spinner 14, which also is a right circular cylinder in this example. At the bottom end of the cylindrical housing 12 the housing inner wall includes an exit orifice 34, the outer edge of which lies along a tangent to an interior circumference within an exit region at the lower end of the shear gap. At the tangents along which the inlet orifice 22 and exit orifice 34 lie, the circumferential flow velocity about the spinner 14 substantially matches the input and output flow rates to reduce acceleration and deceleration effects in an optimized design. However, practical systems that have not used this optimized matching of velocities have not been observed to have deleterious effects on the blood.

As seen only in the sectional view of FIG. 3, the inlet flow of blood passes first through a converging section 26 and then through a straight section 28 having a length at least five times as great as the cross-sectional dimension of the inlet orifice 22. The exit orifice 34 couples to a curved diverting channel 36 (FIGS. 3 and 4 only) which is so shaped as to avoid the introduction of a curvature of opposite sense to the flow within the housing 12, thus providing an alternative example of the manner in which flow may be achieved for either inlet or outlet orifices. The width of the orifice should not exceed the gap dimension. The orifice dimension in elevation, however, may be made substantially larger than the gap dimension in order to adjust inflow velocity or increase scavenging efficiency at the outlet. The inlet flow sections 26, 28 and outlet channel 36 may be molded, in part, with the housing 12 and completed by complementary halves which are affixed thereto.

The cylindrical housing 12 is completed by an upper end cap 40 having an end boss 42, the walls of which are nonmagnetic, and a bottom end housing 44 terminating in a plasma outlet orifice 46 concentric with the central axis. The rotary spinner 14 is mounted in a vertical position between the upper end cap 40 and the bottom end housing 44. The spinner 14 comprises a shaped central mandrel 50, here 1"(2.54 cm) in diameter, preferably of a light weight, strong, impermeable synthetic resin material such as high density polypropylene. To simplify molding it may be made in two separate pieces (not shown) that are joined together. The outer surface of the central mandrel 50 is shaped to define a series of spaced apart circumferential grooves 52 separated by annular lands 54 which lie uniformly in the plane of the cylindrical outer periphery of the mandrel 50. The surface channels defined by the circumferential grooves 52 are interconnected by four longitudinal grooves 56 regularly spaced in quadrants about and extending almost the entire length of the mandrel 50. At each end of the mandrel 50, these grooves 56 are in communication with a central orifice or manifold 58 (best seen in FIGS. 2 and 3) concentric with the central axis, via one of a set of four radial conduits 60 disposed in the same quadrant positions. The grooves 56, orifice 58, and conduits 60 are of sufficient cross-sectional area to avoid imposing a restriction on the flow of filtrate. Also, the circumferential grooves 52 and longitudinal grooves 56 are large enough in cross-section so that there is no substantial difference in pressure drop for fluid regardless of where it transfers through the membrane. In another sense, the pressure drop variations should not be more than a sensible fraction of the transmembrane pressure for high performance operation. Relatively close spacing of the circumferential grooves 52 also is desirable for this uniformity. Two longitudinal lands 61 extend along the mandrel 50 in symmetrical spacing to the longitudinal grooves 56. Thus the mandrel 50 is inherently balanced about its central axis and may be spun at high speed without instability.

The surface of the rotary spinner 14, which is about 3"(7.5 cm) in length, is covered by a cylindrical membrane 62, such as a commercially available filtration membrane of the type sold under the designation polyvinylidine fluoride by Millipore. The membrane 62 has a nominal pore size of 0.6 μm, but other pore sizes may alternatively be used (the range for plasma typically being 0.4 to 0.8 μm). The total surface area of the cylindrical membrane, in this example, is approximately 50 cm$^2$, which is substantially more than an order of magnitude less than the membrane surface area utilized in prior art systems for recovering about 30 to 50 ml/min of plasma.

At its upper end, the rotary spinner 14 is mounted in the upper end cap to rotate about a pin 64 which is press fit into the end cap 40 on one side, and seated within a cylindrical bearing surface 65 in an end cylinder 66 attached to or forming an integral part of the rotary spinner 14. The lower end of the pin 64 protrudes into a small chamber adjacent the bearing surface 65 so that the pin end does not dig into the end cylinder 66. The end cylinder 66 is partially encompassed by a ring 68 of magnetic material (e.g. 440 C stainless steel of Rockwell hardness 45 to 50 or a molded ceramic magnet) utilized in indirect driving of the spinner 14. For this purpose, a drive motor 70 exterior to the housing 12 is coupled to turn an annular magnetic drive member 72 which partially surrounds the nonmagnetic end cap 40. The drive member 72 includes at least a pair of internal permanent magnets 74 in spaced apart, facing relation to the magnetic ring 68 in the end cylinder, but centered below the midpoint of the ring 68 along the vertical central axis. As the annular drive member 72 is rotated, magnetic attraction between the ring 68 interior to the housing 12 and the magnets 74 exterior to the housing locks the spinner 14 to the exterior drive, causing the spinner 14 to rotate without slippage. Moreover, the vertical displacement between the magnets 74 and ring 68 imposes a constant downward force on the spinner 14. A rotational speed of 3600 r.p.m. is used in this example, although significantly higher rotational rates can be used where other parameters are varied or where there is less concern with a minor amount of hemolysis. The given configuration may be operated up to 5550 r.p.m., for example, without substantial hemolysis. Belt drives or gearing (not shown) coupled to the drive motor 70 may be used to step up the rotational speed of the spinner from the nominal rotational rate of the motor 70.

At the lower end of the rotary spinner 14, the central outlet orifice 58 communicates with a central bore 76 in an end bearing 78 concentric with the central axis. The end bearing 78 is seated in the bottom end housing 44 and includes an intermediate tapered side surface 79 that diverges in the downward direction. An end bearing seat is defined by a narrowed concentric throat or internal shoulder 80 forming the lower edge of a central opening 82 in the lower end of the bottom end housing 44. Where the material of the spinner 14 is too soft or yielding, wear at the bearing 78 may be excessive or the seal might otherwise become inadequate for the entire duration of use. In such event a small insert (not shown) of the same internal profile but of harder material may be inset into the spinner 14 in this region to insure maintenance of the seal. End seals or O-rings (not shown) might alternatively be used to provide thrust bearing seals.

The central opening 82 communicates with the plasma outlet orifice 46. A radial bearing surface is defined by the cylindrical upper portion 83 of the end bearing 78, which fits within a mating surface of the central opening 82. As the spinner 14 rotates the end bearing 78 is mechanically urged downwardly on the shoulder 80 region by the magnetic coupling, forming an end seal. If wear occurs the integrity of the seal is maintained, although a properly configured device has a much longer useful life capacity, in terms of wear, than will be required in practice.

The lower end of the spinner 14 body also includes a concave surface 84 facing the opposing end wall, to increase the volume about the end bearing 78. This configuration at the lower end of the spinner aids the capture of entrained air and the formation of a stable bubble about the lower rotary seal to enhance the integrity of the seal and limit heat transfer to the blood flow that might contribute to hemolysis. Minimum blood-air interface areas exist at both ends of the housing 12, when bubbles are trapped at these regions, because the longitudinal ends of the spinner 14 are disposed close to the adjacent end walls (e.g. here less than 0.02"(0.05 cm). The concave surface 84 need not be employed. In addition the reduced diameter of the end cylinder 66 relative to the spinner 14 aids both in the capture of air and in the reduction of gap size without increasing shear stress on the blood. Turbulence in the end regions can induce hemolysis into the plasma retained in the blood flow mass and intensify sealing problems.

In operation, with the rotary spinner 14 rotating at the 3600 r.p.m. rate chosen in this practical example, whole blood is fed through the inlet orifice 22 in a low acceleration and deceleration flow path that commences with tangential entry into the shear gap between the outer surface of the spinner 14 and the inner wall 24 of the housing 12. Circumferential velocity is imparted by viscous drag on the blood layer that is in contact with the outer cylindrical membrane 62 on the rotary spinner 14, so that the spinning action creates a flow about and with the spinner 14.

Ingress of whole blood is preferably at a rate matching the average circumferential velocity in the region of the inlet orifice 22, so as to avoid abrupt shock and sudden acceleration. Although matching of blood inlet flow in this manner is desirable, it is not necessary to maintain a precise relationship because in practice no adverse effects have been observed with a range of inlet flow rates and geometries in plasmapheresis systems of the general character of FIG. 1. The action of viscous drag then provides acceleration, without damage to the blood. Stabilization is quickly achieved as the internal volume between the inner walls of the housing 12 and the outer surface of the rotary spinner 14 is filled. Prior to stabilized operation and plasma outflow, air in the system is forced out through the membrane 62, moving rapidly inwardly through the circumferential grooves 52, the longitudinal grooves 56 and the radial conduits 60 to the central bore 76 in the end bearing 78 to the plasma outlet orifice 46. Plasma immediately begins to follow. The flow of blood may be preceded by a small volume of saline solution in the operation of an integrated system. Centrifugal forces are kept above 50 gravities at an approximate minimum and below 445 gravities at an approximate maximum for the stated configuration and operating conditions. These are not fixed limits, however, inasmuch as flow rates, residence times, and other parameters may be varied for particular applications. For example, if the centrifugal force is lowered below 50 gravities the throughput rate will be reduced significantly but can still be advantageous. Concurrently, the entire cylindrical shell of blood moves longitudinally downward at essentially constant velocity in the shear gap. These conditions alone do not assure high efficiency filtration or non-traumatic handling of blood.

The critical and unstable characteristics of blood arise from both chemical and physical factors, and disruptive effects can easily occur in a high speed, high shear system. Blood has a tendency to adhere to and cover surfaces having foreign characteristics, unless proper movement is maintained. Normal whole blood has a hematocrit of 37 to 54 with a viscosity ($\mu$) in the range of 4 to 5 centipoise at a density ($\rho$) in the range of 1.0 grams per centimeter$^3$. The viscosity of the flow during plasmapheresis, however, markedly increases, because the mass of formed elements without substantial plasma, and particularly the red cell pack, is thixotropic in character. Maintenance of proper flow conditions for these and other reasons, involves due attention to all of the parameters affecting the separation of blood.

The inflow rate of the blood (here about 60 to 100 ml/min) and the internal volume available for blood flow, determine the residence time of the blood within the system. The residence time is typically of the order of 3 seconds in the given example. In one practical system, with a spin rate of 3600 r.p.m., a diameter of 1"(2.54 cm) for the cylindrical membrane 62, and a radial gap of 0.024"(0.06 cm), a shear level of about 8000 sec$^{-1}$ and a centrifugal force of 190 gravities are imposed on the blood passing through the shear gap region. Thus in accordance with the shear principles previously discussed, platelets, leukocytes and other formed elements in the blood are kept in motion across the membrane surface and do not tend to adhere to or plug the pores of the membrane as plasma passes through. It is of significance, relative to effective use of the shear principle, that high shear rates are created without involving either the very small gapes or excessively high flow or recirculation rates normally accompanied by concomitantly high flow resistance, as used in the prior art. Cell packing and concentration polarization, normally present in other systems, are obviated and have minimal effects on the membrane filtration action. In fact, it has been found that even though pinholes may exist in the membrane noticeable red cell concentration or hemolysis is not present in the plasma outflow. The efficiency of plasma transport through the membrane 62 is extremely high throughout an entire cycle of operation. The sole source of the transmembrane pressure in this instance is the static pressure within the system, inasmuch as the velocity components induced by viscous drag tend to oppose the inward motion. Nevertheless, static pressure of the blood flow itself is adequate not only to provide the needed transmembrane pressure, but to cause flow of the plasma filtrate into the surface channels defined by the circumferential grooves 52, from which the plasma is collected into the central orifice or manifold 58 via the longitudinal grooves 56 and the radial conduits 60.

Plasma flow from the system is derived at a rate of about 45 ml/min in this example, given a blood flow of approximately 100 ml/min depending on hematocrit, thus being consistent with the rate at which whole blood may be taken from a donor and the packed cell mass with residual plasma may be returned to the donor.

Figure 5:
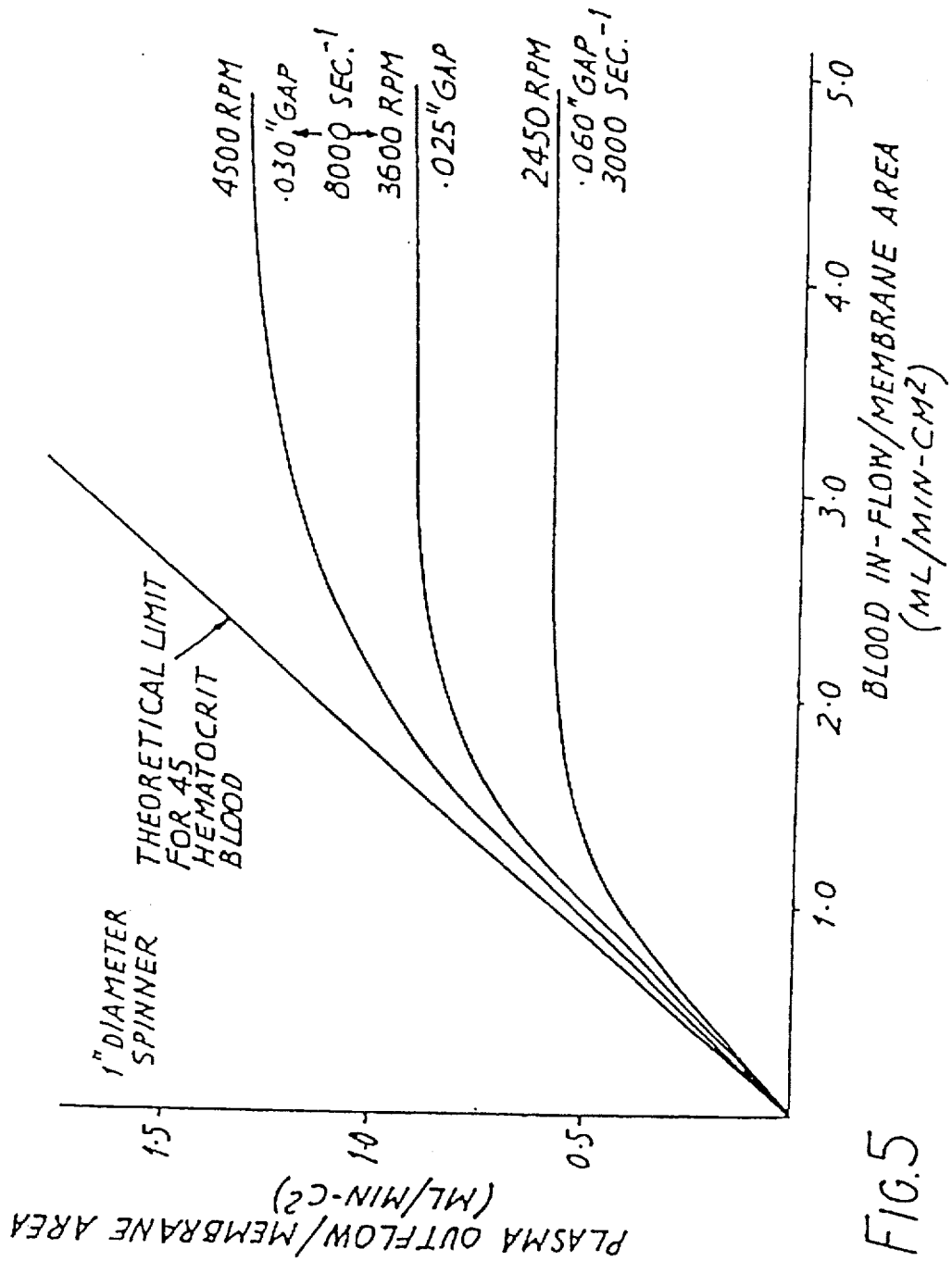
FIG. 5 is a graph of plasma flow per unit area as the ordinate vs. blood flow per unit area as the abscissa for different values of shear in systems in accordance with the invention.

The combination of stratification under centrifugal force and membrane filtration is demonstrably superior. Recoveries in excess of 90% of plasma have been achieved. FIG. 5 shows actual performance results in which attainable quality plasma flux per unit membrane area has been plotted against blood inflow rate similarly normalized. The initial slope of all curves is determined by the inlet blood hematocrit. Therefore, in order to put a great many experimental data taken from various runs with different blood sources on a common plot all data has been corrected to the typical 45 hematocrit where the initial slope is theoretically:

$$\frac{\Delta(P/Am)}{\Delta(B/Am)} = 0.55$$

where P=plasma rate
B=inflow blood rate
Am=membrane area

Note that plasma rates become asymptotic with increasing blood flow although the level of the asymptote increases with increasing r.p.m. as expected. Theoretical prediction of the asymptotic value is difficult. It has beem empirically demonstrated, however, that the value increases more rapidly as a function of centrifugal force (when shear rate is held constant by varying the gap spacing proportionately with r.p.m.) than it does for increasing shear with constant centrifugal force (by varying the gap only). In either case, those skilled in the technology will recognize that the current state of the art provides plasma recoveries, per unit of membrane area, that are usually less than 0.05 ml/min-cm$^2$. In the current art, flat plate systems are producing, at best, about 55 ml/min with a 1400 cm$^2$ membrane area (0.039 ml/min-cm$^2$), while hollow fiber systems are producing about 22 ml/min with a 1700 cm$^2$ membrane (0.013 ml/min-cm$^2$). In contrast, with the 1" spinner, 50 cm$^2$ membrane and the shear gap and rotational rate of the system of FIGS. 1–4, the flow rate is easily stabilized at about 0.9 ml/min-cm$^2$ and can be taken higher. Applicant has thus provided, approximately an order of magnitude improvement over prior techniques used in this intensely worked art.

Systems constructed in accordance with the invention and used to generate the performance data of FIG. 5, provide a plasma filtrate that is protein rich, golden in color, and essentially completely free of hemolysis and any trace amounts of formed elements. The hematocrit of the packed cell mass that moves out of the exit orifice 34 is in the range of 75 to 90% and exhibits only minimal if any increment of free hemoglobin over normal biological levels. The dual capability for high efficiency recovery of plasma and the return of high hematicrit flow to a donor will be recognized as extremely significant by those skilled in the art.

The extremely low blood priming volume, achieved by virtue of very low membrane area together with small blood film thickness, will be appreciated as a significant medical advantage in certain therapeutic applications of the device. In the example of a practical device the total hold-up volume of the device including entrance orifices and headers, but excluding the remainder of the blood lines and bags, is only approximately 5 ml in the collection device.

Further, the cost savings inherent in using a small area of expensive membrane are also evident for disposable systems. The problem in plasmapheresis, for the practical application that is described herein, is to transfer a normal donor supply of 2–3 units of blood through a small disposable unit which will reliably function to recover 60% to 90% of the protein rich plasma and return the high hematocrit flow readily to the patient without damage to red blood cells, leukocytes or platelets. In accordance with the invention, the spinner surface velocity V$_s$ and gap (d) are selected, relative to the entering blood viscosity (μ) and density (ρ) such that high centrifugal force and shear values are established, but (in order to protect red cells) not in excess of 15,000 sec$^{-1}$, and with the Reynolds number being below 2000. Given that:

$$V_S = \pi \times D \times \frac{(\text{r.p.m.})}{60},$$

in/sec., where $D$ is the spinner diameter in inches and the (r.p.m.) is the rotation rate per minute, $$S = \frac{V_S}{d} = \text{shear in sec}^{-1}$$

$$(\text{r.p.m.})_{max} = \frac{.75}{D} \left[ \frac{(\mu/\rho) S_{max}}{10\rho} \right]^{1/2} \times 10^3 \quad \text{(Equation 1)}$$

$$\left[ \frac{\pi}{60} \frac{D(\text{r.p.m.})}{S_{max}} \right] \leq d \leq \left[ \frac{7.5 \times 10^3 (\mu/92)}{\alpha D(\text{r.p.m.})} \right] \quad \text{(Equation 2)}$$

In the above, μ is in units of poise, d and D are in inches and S$_{max}$ is the maximum value of blood shear rate qualified below. The value of μ, the coefficient of absolute viscosity, for an "ideal" Newtonian fluid, where viscosity is not a variable, is 0.5. However, because of the high viscosity and thixotropic characteristic of blood wherein viscosity varies with shear rate and is an exceptionally strong function of cell concentration, the velocity profile across the gap between the spinning wall and the stationary wall is not a linear function. It has been determined experimentally that an approximate value of α=0.9 may be used. The significance of Equations (1) and (2) above may then be interpreted as follows. If one elects the maximum value of (r.p.m.) given by Equation (1) then d is constrained to a single value for which Equation (2) is an equality. For all lower values of (r.p.m.) the inequalities of Equation (2) permit a range of choices for gap dimension d.

Figure 6:
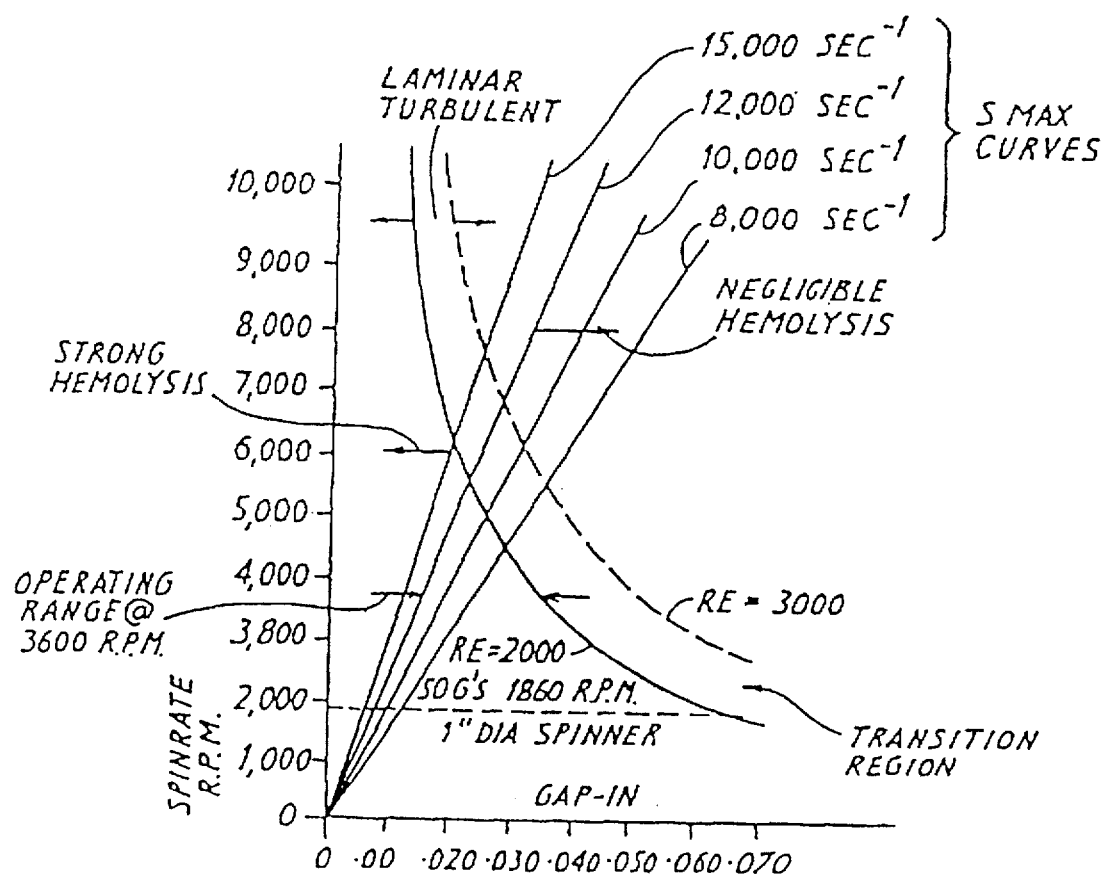
FIG. 6 is a graph depicting the relationship between shear and Reynolds number for different values of rotational rate as the ordinate and gap as the abscissa relative to the arrangement of FIG. 1.

Following these considerations, and constrained by the practical need for a small, low cost and disposable spinner, the useful and conservatively safe operating values for critical parameters fall within relatively small ranges. Adopting a conservative limit of 12,000 $sec^{-1}$ for shear in order to limit hemolysis to negligible levels for a 1" spinner, for example, the gap between the spinner and the containment wall in a practical device is 0.0155" to 0.03711" given a rotational rate of the spinner at 3600 r.p.m., as seen in FIG. 6. For a maximum rotation rate of 5550 r.p.m. the gap dimension is 0.024" and one is operating at the marginal level at which hemolysis may occur, flow may arise. This is not to say, however, that the operation of the system is in any sense critical, inasmuch as devices constructed in accordance with the invention maintain laminar flow and achieve stratification of the plasma layer substantially throughout the length of the spinner. As illustrated in the example above, it is, of course, feasible to maintain laminar flow by increasing the Further consideration should be given to the graph of FIG. 6 in terms of the interacting relationships that are to be observed with blood as the liquid suspension system. With the gap dimension (d) as the abscissa and rotational rate (r.p.m.) as the ordinate, a linear shear line may be drawn from the common base point for the predetermined maximum shear ($S_{max}$) that will be tolerated. Lines are shown for shear rates of 8000 $sec^{-1}$, 10,000 $sec^{-1}$, 12,000 $sec^{-1}$, and 15,000 $sec^{-1}$ at the highest of which levels greatest hemolysis occurs, although still found to be at an acceptable level for many applications. Increases in hemolysis are first detected at about 12,000 $sec^{-1}$, but hemolysis is not significant until 14,000 $sec^{-1}$ is reached, and becomes very significant above 15,000 $sec^{-1}$. The linearity of the shear rate follows from the expression for shear previously given, and because the non-linear characteristics do not strongly affect plasmapheresis applications. The slope of the shear line will be substantially steeper for a stable, non-critical liquid. Although as previously noted, the velocity gradient may well not be linear, the non-linearity appears to be operative in a favorable sense because, lighter plasma strata appears to be subjected to high shear. There are only minor increases in hemolysis levels, tolerable for many applications, when nominal shear rates exceed the approximately 6000 $sec^{-1}$ to 7000 $sec^{-1}$ limits encountered in the prior art. These latter values correspond to the shear stress levels of 240 to 280 dynes/$cm^2$ for normal human blood as reported by Blackshear, P. L. Jr. et al in "Fluid Dynamics of Blood Cells and Applications to Hemolysis", NTIS Report PB-243 183, pp. 95–102 (October 1974), see also Chien, S. et al, "Shear-Dependent Deformation of Erythrocytes in Rheology of Human Blood", Amer. J. Physiol., V. 219, p. 136 (1970).

There is a generally inverse and non-linear relationship between r.p.m. and d with respect to Reynolds number. For a given viscosity (e.g. blood at 4 centipoise) a curve of opposite slope representing Re≦2000 intersects the shear lines at intermeidate points. The r.p.m. value assumes a certain spinner diameter (here 1") and thus centrifugal force, and it will be recognized that the curves are merely offset by any adjustment of the spinner size. Although centrifugal force has some influence at even low r.p.m. values, practical systems require an optimum combiation of small size, low cost, high recovery of plasma and limited time demands on the plasma donor. Thus a rotational rate, for a particular spinner diameter, that is sufficient to give in excess of 50 gravities will typically be used in practical systems.

These controlling factors dictate the configuration, throughout the entire length of the device, including entry and exit regions and because it is preferred to utilize, for disposable plasma separator systems, a compact structure. In a compact structure, however, introduction of blood into the gap region, and extraction of high hematocrit flow at the outlet end are effected by tangential paths which either include a stabilizing section or avoid introduction of reverse curvature in the flows. The outlet apearture and the exit region may be modified in particular ways to accommodate the increased viscosity of the thickening flow mass in this region. The outlet aperture cross-section need not be symmetrical, for example, so that area can be increased by extending the height (elevation) dimension along the central axis. Also, the shear gap may be increased, due to the increasing viscosity of the thickening cell mass near the exit flow. Thus in the system of FIGS. 1–4 the gap width may be enlarged in curvilinear fashion, along with or separately from the height, to further increase the cross-sectional area of the exit orifice and improve scavenging of red cells.

The length of spinner which is covered by membrane is preferably short, because of the cost of the membrane material. For 50 $cm^2$ of membrane, which is sufficient for recovering 20–50 ml/min of plasma from a given donor, depending upon hematocrit and blood supply rate, the membrane carrying length of a 1" spinner is less than 3". Despite this relatively short length, the residence time is fully adequate for high recovery rates. The example of a low cost disposble given herein processes 3 units (1500 ml) of flow to collect 600–700 ml of plasma, thereby giving at least a 75% recovery fraction. The length and total residence time can of course be increased when desired for particular processes. In addition, the bloow flow can be pressurized so that transmembrane pressure is increased and the filtration process enhanced.

It will be appreciated here that the drawings are not to scale and that shear gaps, as well as variations in shear gaps, have been depicted only generally to illustrate the principles involved.

The outer wall can serve not only as a stationary shear boundary but also perform other functions, as depicted in FIGS. 7 and 8. It is not a conventional procedure to preserve frozen concentrated red cells in an antifreeze solution (ethylene glycol) whereby the cells may be frozen but are protected by the non-frozen liquid matrix from crystallizing and breaking. The red cells must be washed free of the solution in which they are suspended after they are returned to a useful temperature range. While the frozen red cells may be stored in a relatively pure state by the use of a prefiltration process, such procedures are difficult and expensive. Usually, therefore, the concentrate is accompanied by white cells and white cell aggregates which adhere together and form a slimy, floating substance that is colloquially referred to as "snot". Removal of the white cell aggregates along with the toxic carrier is a prime objective. The fractionation system of FIGS. 7 and 8 utilizes the basic structure of the system of FIGS. 1–4, but with further features to enable clear separation of concentrated red cells from fall such extraneous matter.

The spinner 14 is driven as previously described, but is somewhat different in interior configuration and in the flow passageway system. The principal length of the spinner 14 is a hollow cylindrical body, the outer wall 90 of which includes circumferential grooves 52 as previously described, interconnected by two longitudinal grooves 92 of adequate cross-sectional area to permit unimpeded flow. The hollow body may readily be fabricated by molding two or more parts that are threaded or bonded together, and represents savings in material as well as mass. At the lower end of the spinner 14, each longitudinal groove 92 communicates with a short central axial manifold 94 via a different radial conduit 96. The upper end of the spinner 14 rotates on an axial bearing 98 set into the cylindrical housing 12, and a magnetic ring 100 concentric with the central axis is remotely driven as previously. For higher torque applications separate elements of high coercivity ceramic magnet (not shown) may be used instead of the magnetic ring. The vertical offset between the spinner magnetic structure and the associated drive is different from the arrangement of FIGS. 1-4, in that the outer drive is centrally positioned along the height of the ring 100. Thus the biasing force exerted by the magnetic field suspends the spinner 14 between bearings at each end, creating a predetermined clearance between the lower end of the spinner 14 and the bottom horizontal inner wall of the housing 12 and eliminating any thrust loads. A rotary seal at the lower end is provided by a radial O-ring 102 disposed about an apertured end bearing 104 seated in the housing and seated in a circumferential groove 106 in the side walls of the central axial manifold 94. Even though the spinner 14 may slide down relative to the O-ring 102 prior to installation of the separator device in a system, the spinner 14 is quickly drawn to and held in the proper clearance position by the magnetic biasing force when in operation.

In this example, the spinner 14 is covered with a surface membrane or filter 108 having a pore size of approximately 70 µm for the passage of ethylene glycol, white cell aggregate and saline solution. A range of pore (or other aperture) sizes of 60-100 µm is generally suitable for this application, but can be varied depending on such factors as special characteristics of the flow mass and the percentage of red cells to be lost through the filtering element. Where the mass contains no or little white cell aggregate the pore size can be about 0.6 um, for example. The cylindrical housing 12 includes a porous cylindrical inner wall 112 at least coextensive with the length of the membrane or filter 98. It is preferred to use a porous synthetic material such as sintered polypropylene, polyethylene or polytetrafluoroethylene. With larger size apertures being usable, however, the wall 112 may alternatively comprise one or more screens of fine mesh, such as stainless steel, or an element in which apertures have been formed, as by a laser beam. In any event the wall 112 has sufficient porosity that a saline solution may permeate rapidly in the desired proportion to the flow volume of the concentrated red cells and accompany matter. This proportion may range from somewhat less than 1:1 to 20:1 for such flow masses. The inner wall 112 is separated from an outer wall 114 defined by a part of the housing 12, and the intervening space defines a plenum 116 to which is coupled an inlet 117 for saline solution. The inlet flow mass is injected via an inlet orifice 118 into the shear gap between the spinner 14 and the inner wall 112 of the housing 12, and washed red cells are derived at the lower end of the shear gap at an outlet orifice 119. If desired, the saline solution flowing into the system may be substantially pressurized within the plenum 116 so as to increase or control the throughput rate of the saline solution.

As the spinner 14 rotates, saline solution constantly permeates in a high area cross-flow through the porous wall 112 into the shear gap in which the red cells are being spiraled downwardly along with the toxic carrier and white cell aggregate. Thus at the upper end of the spinner 14, concentrated ethylene glycol begins to pass concurrently as filtrate through the membrane 108 along with gradually increasing amounts of cross-flowing saline solution. The constant introduction of saline solution about the outer periphery then acts initially on the least contaminated portion of the blood cell mass. As the saline solution passes through the entire thin shell flow it intermixes with an increasing proportion of ethylene glycol and white cell aggregate, acting in a sense as a diluent while also carrying this lighter matter inwardly. Toxic carrier along with white cell aggregate in heaviest concentration and saline solution is most diluted form encounter the membrane 108 and are filtered out of the system. The relatively large pore size of the membrane 108 permits ready passage of the oleaginous white cell aggregate, while the toxic carrier and saline solution are washed out with even grater facility. A minor fraction (typically less than 1-2%) of red cells also may wash out through the large pores, but this can be accepted in exchange for elimination of the mucous white cell mass. The cross flow of the purifying saline solution relative to the spinning cell mass, being distributed across a high area but having only a short path length in the radial direction, is thus extremely efficient. Newly injected saline solution constantly moves across the entire flow area, and there is no possibility of formation of static or stagnant pool of toxic carrier. At the outlet orifice 119, therefore, only purified red cells leave the system from the shear gap region. Typically, the volume of saline solution, per unit volume of incoming combined red cell, white cell aggregate and ethylene glycol, will be sufficient to insure that only a minor proportion of saline solution is present in the red cell outflow. If desired, however, the volumetric relationship between the incoming flow and the saline flow can be adjusted to provide a controlled hematocrit in the red cell outflow.

Figure 9:
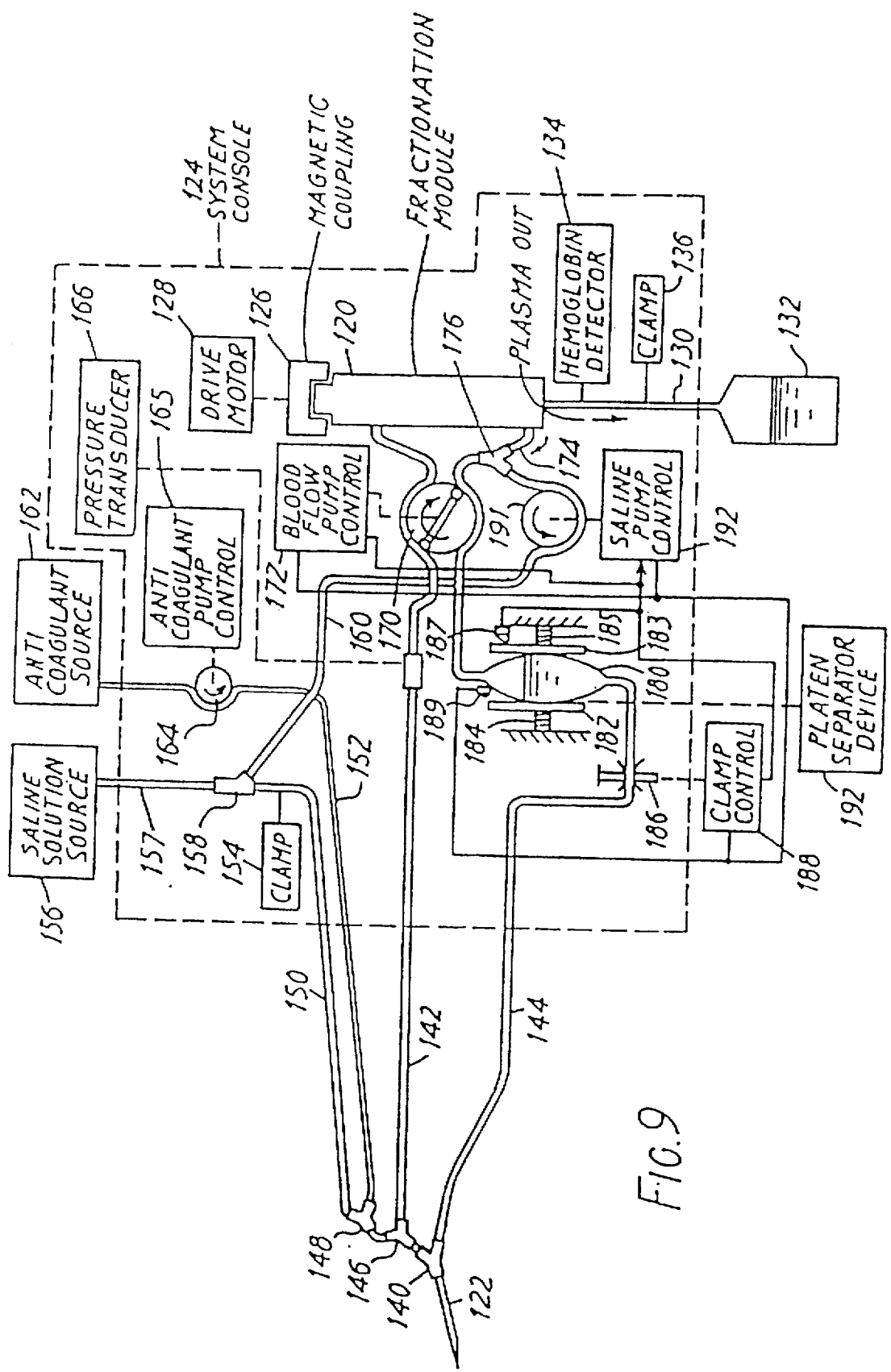
FIG. 9 is a combined schematic and block diagram representation of a first control and instrumentation system for plasmapheresis in accordance with the invention.

FIG. 9 is a generalized and schematic representation of a system in accordance with the invention that provides a completely disposable blood handling set employing a fractionation module 120 based on the shear principle with a single needle implantation device 122, this being the instrument of choice for donor comfort in blood fractionation applications for human donors. All portions of the system which come into contact with blood flow, or separated constituents of blood, are of low cost and disposable character, while blood pumping, sensing and control functions are carried out externally of the distribution system. The fractionation module 120 is simply clamped or positioned in place by a suitable bracket or other means (not shown) on a system console 124, within which motors and instrumentation are mounted, although these are shown in schematic or block diagram form inasmuch as the configuration of the console 124 is not significant for purposes of the present disclosure. When in position, the upper end of the module 120 fits within a magnetic coupling 126 which is driven by a drive motor 128, thereby to rotate the spinner within the module 120.

Plasma flow from the bottom of the module 120 proceeds through a length of flexible tubing 130 to a plasma collection bottle 132, past an optical hemaglobin detector 134 and a tubing clamp 136. The hemaglobin detector 134 may be any suitable commercially available device that is optically sensitive to the passage of material having the optical characteristics of hemaglobin in the blood, because the presence of a significant amount of blood indicates a leakage or failure in the system. The detector may generate a signal which activates a display (not shown) for the operator, so that the clamp 136 can be manually closed, or may provide a signal to an automatic system for activating the clamp 136 by solenoid control.

At the donor end of the system, the intravenous disposable needle 122 couples through a first junction 140 to an inlet blood flow line 142 and a return line 144, both of these lines being of flexible, disposable tubing. The coupling to the inlet blood flow line 142 is made through a second junction 146, the alternate port of this Y configuration junction being coupled to a third junction 148 which receives saline solution on a saline priming line 150 at one port, and an anticoagulant on an anticoagulant delivery line 152 at the other port. The saline priming line may be closed by the operator at a clamp 154 or automatically if desired, when the priming function has been carried out. A source 156 of saline solution is gravity fed through a source line 157 to a connector 158 which couples both to the saline priming line 150 and to a saline injection line 160 that is used in a manner described hereafter. An anticoagulant source 162 also elevated above the system, feeds through the anticoagulant, delivery line 152, which is of smaller diameter than the blood tubing, past a roller or peristaltic pump 164 which is adjustable by a pump control 165 so as to provide a selected rate of delivery of anticoagulant, depending upon the hematocrit and blood delivery rate of the donor. The anticoagulant pump control 165 may be operator adjustable, although a microprocessor controlled system may also be utilized, including means for sensing blood flows at various points and adjusting the rate of anticoagulant delivery within limits so as to maintain the blood flow. The donor and implanted needle 122 should also be understood to be physically elevated with respect to the system, so that blood flow on the inlet line 142 is initiated and at least partially maintained by gravity in order to protect the donor from suction at the vein.

The inlet blood flow line 142 passes a pressure transducer 166 which is of the type that has a sterility barrier and senses pressure variations in the flexible tubing without occluding the line or introducing a separate flow path. The pressure transducer 166 generates a signal which can be utilized to control an analog display for the operator, because the lack of pressure in the system, once started, may indicate a deleterious condition such as displacement of the needle or suction on the line.

The inlet blood flow line passes a roller pump 170, depicted schematically, which is set to an adjustable rate by a blood flow pump control 172, and terminates at the inlet orifice to the fractionation module 120. The same roller pump 170 also is in operative association with a blood outflow line 174 which passes via a Y junction 176 and the pump 170 to a reservoir 180. The reservoir 180 is a flexible disposable container including a bottom outlet to which the blood return line 144 is coupled, and is interposed between a pair of movable platens 182, 183. The platens 182, 183 are movable transversely outwardly in opposite directions against springs 184, 185 as the reservoir 180 fills with blood, because a clamp 186 on the return line 144 blocks outflow from the reservoir 180. When the reservoir 180 is sufficiently filled, a limit switch 187 is actuated by the adjacent platen 183 to indicate that the cell flow is to be returned to the donor. This may be done manually by an operator in response to a signal or display, by stopping the pump 170 and releasing the clamp 186, or the actions may be undertaken by an automatic control system coupled to the blood flow pump control 172 and a clamp control 188. A separate limit switch 189 is positioned to detect when the platens 182, 183 have moved inwardly together to the opposite limit position and have expressed all or substantially all of the return flow to the donor. The springs 184, 185 are depicted only generally, and it will be understood that they may be of the type that provides substantially constant and relatively low force throughout the length of their travel, thus insuring gentle and hemolysis-free return of blood to the donor. Alternatively, a mechnical, pneumatic or hydraulic device may be used for this purpose. It will also be appreciated that the reservoir 180 may include a manually or automatically closeable vent (not shown) for allowing the escape of air from the device. A separator device 192, such as a wedge in the simplest case, is movable manually or automatically between the platens 182, 183 to separate them slightly from the fully closed position.

In operation of the system of FIG. 9, priming of the lines is a conventional safeguard that precedes actuation of the blood flow pump. With the spinner in the fractionation module 120 operating, however, the pump 170 may be turned on after priming, to begin the inlet flow of blood, accompanied by a suitable amount of anticoagulant from the source 162, the amount being related to the volumetric flow of the plasma portion of the total blood flow and being a fraction thereof. With the rate of plasma delivery from the donor of 30 to 50 ml per minute, a typical plasma volume of approximately 600 ml is collected in 10 to 20 minutes. The hematocrit of the donor, as well, as the donor size and weight, and other factors, however, establish that the blood flow rate and plasma contributions of individual donors can vary substantially. Consequently, it is not safe to assume that a specific proportion of return flow exists in relation to the whole blood inlet flow or the plasma extracted. Furthermore, pulsations that tend to be introduced by a roller pump can tend to cause surges within the fractionation module 120, or a momentary disparity between inflows and outflows that causes cellular matter to penetrate through the membrane in the module. Such problems are avoided by the usage of the blood flow pump 170 to control both blood inlet and blood outlet flows, in addition to supplementation of the outlet flow with saline solution via a saline pump 191, the rate of operation of which is adjustable by a saline pump control 192. The roller pump 170 is preferably of the type having a pair of opposed rollers, symmetrically displaced with respect to the lines 142 and 174 respectively, so that each roller engages and disengages the associated line at a given point in time concurrently. Thus, the pulsations which occur upon engagement appear at both the entry and outlet ports of the module 120 and no excess transmembrane pressure appears in the flow of plasma. The coordinated action in effect eliminates pulsations on the membrane at times of momentary interruptions of flow. Consequently there is positive displacement of both inlet and outlet flows, and because the pumping actions are physically determined by the geometry of the roller pump 170, no compensating features need be employed. Furthermore, any differential in the amount of plasma fraction that is extracted at the module 120 can be safely compensated by the injection of saline into the return cell flow. The operator can use the saline pump control 192 to make adjustments in the net rate of the pump so as to limit the maximum output of plasma to a safe level. The pump 170 tends to displace the same volume of outflow solution as inflow solution, for a given rotation, or to displace a fixed proportion other than 1:1 if the tubing sizes are different. The volume of saline made available per revolution is directly translatable to mass, and this replenishment enables precise and reliable control of the amount of plasma that can safely be taken out of the system. A pump, such as the roller pump 170 is advantageously employed for varying the rate of saline injection, but it will also be appreciated that the size of the saline line may also be varied to give a proportional control, with or without the use of the pump 170.

The return flow is not continuous, but only takes place when a predetermined maximum level of blood in the reservoir 180 has been sensed by the limit switch 187. At this time, the blood flow pump 170 is stopped, the clamp 186 is opened, and the platens 182, 183 are thus freed to compress the reservoir 180 gradually. This compression returns the cell mass with saline solution through the return line 144 to the donor at a higher rate, such as 100 to 300 ml per minute. Before resuming inlet flow it is advantageous to separate the platens 182, 183 slightly and momentarily with the separator device 190, which in the simplest case may be a wedge interposed between the platens 182, 183. Release of pressure on the reservoir 180 causes a small amount of the packed cells to be drawn backwards into the reservoir 180, to draw donor blood past the junction 140 so that blood cell remainder is kept from being fed into the module 120 on the inlet line.

It will be appreciated that additional blood flow reservoirs may be utilized, if desired, and that different pumping systems may be employed, particularly where the requirements of a single needle, disposable blood set application need not be met.

Figure 10:
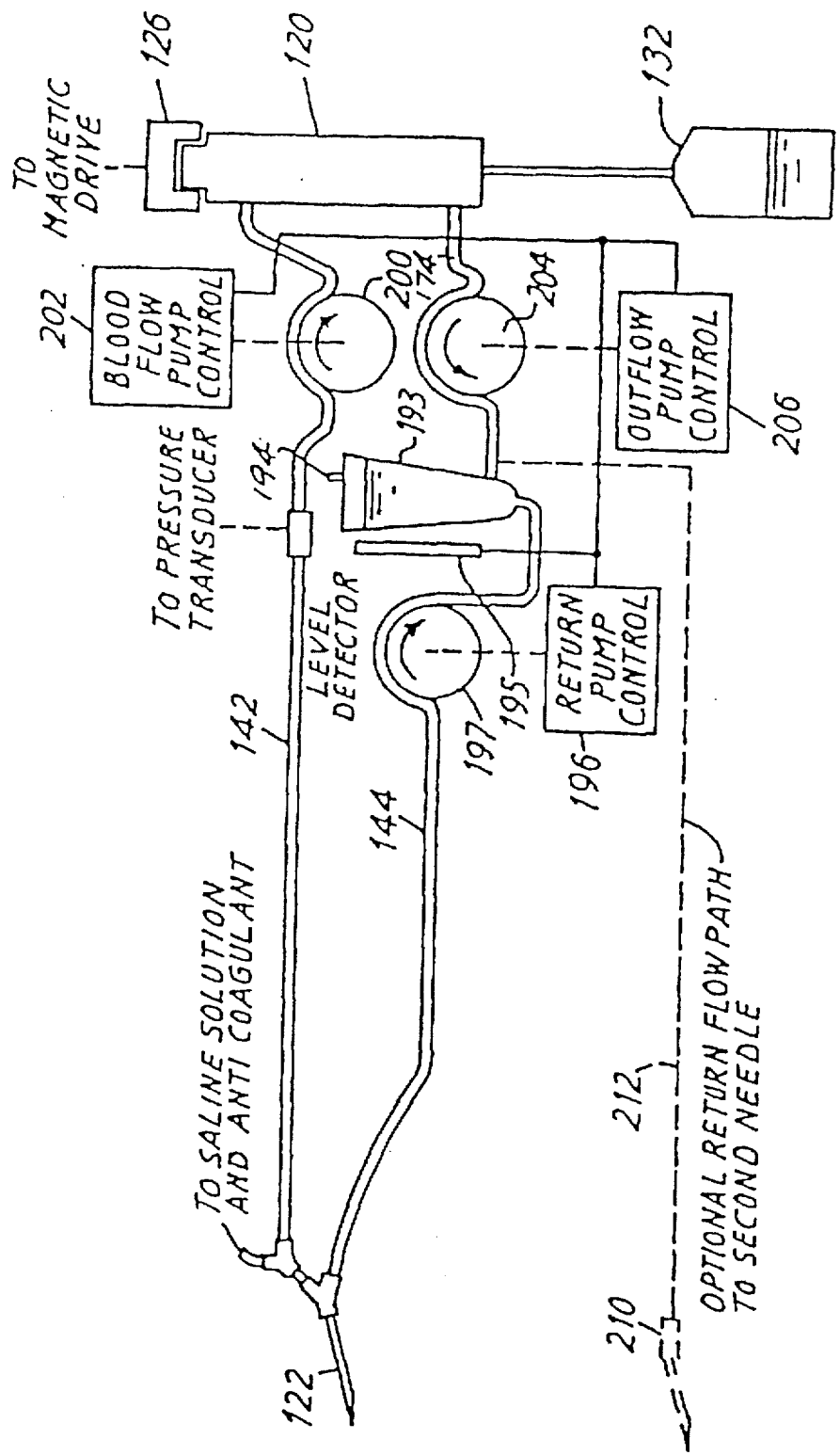
FIG. 10 is a combined schematic and block diagram representation of a different system for plasmapheresis in accordance with the invention.

An example of one such system is shown in FIG. 10, in which elements and devices are numbered as in FIG. 9 and only system variants are shown, with most of the duplicative portions being omitted for brevity. In FIG. 10 the blood outflow line 174 feeds blood cell remainder into a transparent or translucent reservoir 193 having a top vent 194 and a bottom outlet to which the blood return line 144 is coupled. A level detector 195 disposed adjacent the reservoir 193 provides an analog signal to a return pump control 196 which actuates a return roller pump 197 to rotate it in the proper direction (counterclockwise) to return the cell flow to the donor. The return pump control 196 may also be rotated in the opposite direction (clockwise) when blood or saline solution has reached the pump 197 through the return line 144 during priming operations. This rotation feeds solution into the bottom of the reservoir 193 and dispels air from the return line 144 so that there is no danger of returning an air bubble to the donor. A separate blood flow pump 200 and associated control 202 are used at the inlet side of the module 120, while a separate outflow pump 204 and coupled control 206 are used at the outlet side. The two pumps 200, 204 are operated in a selected flow relation (which may be operator or micropocessor controlled) the difference being the plasma flow rate. When the reservoir 193 is filled to a selected level, the signal from the level detector 195 permits manual or automatic stoppage of the pumps 200, 204, and actuation of the return pump 197, until the reservoir 193 contents are returned to the donor. When delivery is complete, momentary reverse actuation of the return pump 197 can be employed to withdraw blood cell remainder from the needle 122 into the return line 144, so that only whole blood passes to the module 120 via the inlet blood flow line 142. Such an arrangement may be used where it is preferred to limit dilution of the plasma protein content by avoiding return of saline solution to the donor.

A further variant of the system of FIG. 10 is shown in an alternate dotted line coupling to a second return needle 210 via a direct tubing 212 connection from the outflow blood pump 204. The double needle enables return flow to be concurrent with inlet flow and a volumetric buffer system such as an intermediate reservoir is not needed. Although less comfortable for the donor, two needle systems are more often used than single needle systems with therapeutic apheresis applications.

While there have been described above and illustrated in the drawings various forms and modifications in accordance with the invention, it will be appreciated that the invention is not limited thereto but encompasses all modifications and exemplifications falling within the terms of the appended claims.

What is claimed is:

1. A method of filtering a fluid suspension having at least one biological cellular component that is characterized by having a nonrigid cell membrane free of a rigid outer cell wall, the cellular component being thereby subject to trauma when stressed, the method comprising the steps of conveying the fluid suspension from a source into a gap defined between a first surface that is located about an axis and a second surface that is concentric with the first surface and that has an attached microporous filter membrane having a pore size to separate filtrate from the fluid suspension to leave within the gap a concentrated suspension of the at least one cellular component that is subject to trauma, holding the first surface stationary while rotating the second surface and, with it, the filter membrane relative to the first surface about the axis at a selected surface velocity, taking into account the size of the gap, to create movement of the fluid suspension within the gap without substantial trauma to the cellular component for inducing transport of the cellular component from the membrane while the fluid suspension is transported to the membrane, conveying filtrate through the microporous membrane to an outlet, withdrawing filtrate from the outlet, and withdrawing the cellular component from the gap.

2. A method according to claim 1 and further including the step of maintaining a selected flow relationship between the conveyance of the fluid suspension into the gap and withdrawal of cellular component from the gap to maintain a desired optimal rate in the withdrawal of filtrate from the outlet.

3. A method according to claim 1 wherein the step of conveying the fluid suspension into the gap includes creating pressure pulsations by a peristaltic pump roller, wherein the step of withdrawing the cellular component from the gap includes creating pressure pulsations by a peristaltic pump roller, and further including synchronizing the peristaltic pump rollers to provide concurrent pressure pulsations to eliminate disparate pressure surges within the gap.

4. A method according to claim 1 wherein the step of withdrawing the cellular component from the gap includes collecting the cellular component in a reservoir, and further including the step of periodically returning the cellular component collected in the reservoir to the source.

5. A method according to claim 4 and further including the step of terminating the conveyance of fluid suspension into the gap and the withdrawal of cellular component from the gap while the cellular component in the reservoir is being returned to the source.

6. A method according to claim 1 wherein the step of withdrawing the cellular component from the gap includes withdrawing the cellular component at a flow rate, and further including the step of introducing an additive solution to the cellular component in a preselected proportion to the flow rate at which the cellular component is being withdrawn.

7. A method of filtering filtrate from a fluid suspension having at least one cellular blood component that is subject to trauma comprising the steps of conveying the fluid suspension from a source into a gap defined between a first surface that is located about an axis and a second surface that is concentric with the first surface and that has an attached microporous filter membrane having a pore size to separate filtrate from the fluid suspension to leave within the gap a concentrated suspension of the at least one cellular blood component that is subject to trauma, and holding the first surface stationary while rotating the second surface and, with it, the filter membrane relative to the first surface about the axis at a selected surface velocity, taking into account the size of the gap, to create movement of the fluid suspension within the gap without substantial trauma to the cellular blood component for inducing transport of the cellular blood component from the membrane while the fluid suspension is transported to the membrane, conveying filtrate through the microporous membrane to an outlet, withdrawing filtrate from the outlet, and withdrawing the cellular blood component from the gap.

8. A method according to claim 7 and further including the step of maintaining a selected flow relationship between the conveyance of the fluid suspension into the gap and the withdrawal of cellular blood component from the gap to maintain a desired optimal rate in the withdrawal of filtrate.

9. A method according to claim 7 wherein the step of conveying the fluid suspension into the gap includes creating pressure pulsations by a peristaltic pump roller, wherein the step of withdrawing the cellular blood component from the gap includes creating pressure pulsations by a peristaltic pump roller, and further including synchronizing the peristaltic pump rollers to provide concurrent pressure pulsations to eliminate disparate pressure surges within the gap.

10. A method according to claim 7 wherein the step of withdrawing the cellular blood component from the gap includes collecting the cellular blood component in a reservoir, and further including the step of periodically returning the cellular blood component collected in the reservoir to the source.

11. A method according to claim 10 and further including the step of terminating the conveyance of fluid suspension into the gap and the withdrawal of cellular blood component from the gap while the cellular blood component in the reservoir is being returned to the source.

12. A method according to claim 7 wherein, during rotation, the surface velocity of the filter membrane is approximately that provided by rotating a one inch diameter body about its axis at 3600 rpm ($3600 \times 1.0 \times \pi/60 = 188.5$ inches per second), or higher.

13. A method according to claim 7 wherein during rotation of the filter membrane a shear rate less than about 15,000 $sec^{-1}$ is generated.

14. A method according to claim 7 wherein the fluid suspension is conveyed into a gap in the range of approximately 0.0155 inch to 0.037 inch.

15. A method according to claim 7 wherein the step of withdrawing the cellular blood component from the gap includes withdrawing the cellular blood component at a flow rate, and further including the step of introducing an additive solution to the cellular blood component in a preselected proportion to the flow rate at which the cellular blood component is being withdrawn.

\* \* \* \* \*